United States Patent [19]

Tohzuka et al.

[11] Patent Number: 5,227,516

[45] Date of Patent: Jul. 13, 1993

[54] FLUORINE-CONTAINING POLYETHER AND NONIONIC SURFACTANT COMPRISING THE SAME

[75] Inventors: Takashi Tohzuka; Sueyoshi Ishikawa; Ikuo Yamamoto, all of Osaka, Japan

[73] Assignee: Daikin Industries Ltd., Osaka, Japan

[21] Appl. No.: 808,927

[22] Filed: Dec. 18, 1991

Related U.S. Application Data

[60] Division of Ser. No. 556,419, Jul. 24, 1990, which is a continuation-in-part of Ser. No. 340,481, Apr. 19, 1989, abandoned.

[30] Foreign Application Priority Data

Apr. 19, 1988 [JP] Japan .................. 63-97682

[51] Int. Cl.$^5$ ............................. C07C 69/66
[52] U.S. Cl. ............................. 560/182; 560/184
[58] Field of Search .......................... 560/182, 184

[56] References Cited

U.S. PATENT DOCUMENTS 3,644,492 2/1972 Bartlett .................. 560/184
4,079,084 3/1978 Houghton ............... 560/184

FOREIGN PATENT DOCUMENTS 2344585 10/1977 France.

OTHER PUBLICATIONS

CA 100(20):162230k 1984.

Primary Examiner—Paul J. Killos
Attorney, Agent, or Firm—Birch, Stewart, Kolasch & Birch

[57] ABSTRACT

A fluorine-containing polyether of the formula:

$$R_f\text{—X—A} \quad \quad (I)$$

or $$\text{A—X—}R'_f\text{—X—A} \quad \quad (II)$$

wherein $R_f$ and $R'_f$ are each a linear group containing a perfluoroalkyl polyether group, X is —CF$_2$COO—, —C$_2$F$_4$COO— or —CF$_2$CF$_2$— and A is a group containing a polyalkylene glycol group. The polyether can be used as a nonionic surfactant which is compatible with a perfluoroalkyl polyether.

2 Claims, 1 Drawing Sheet

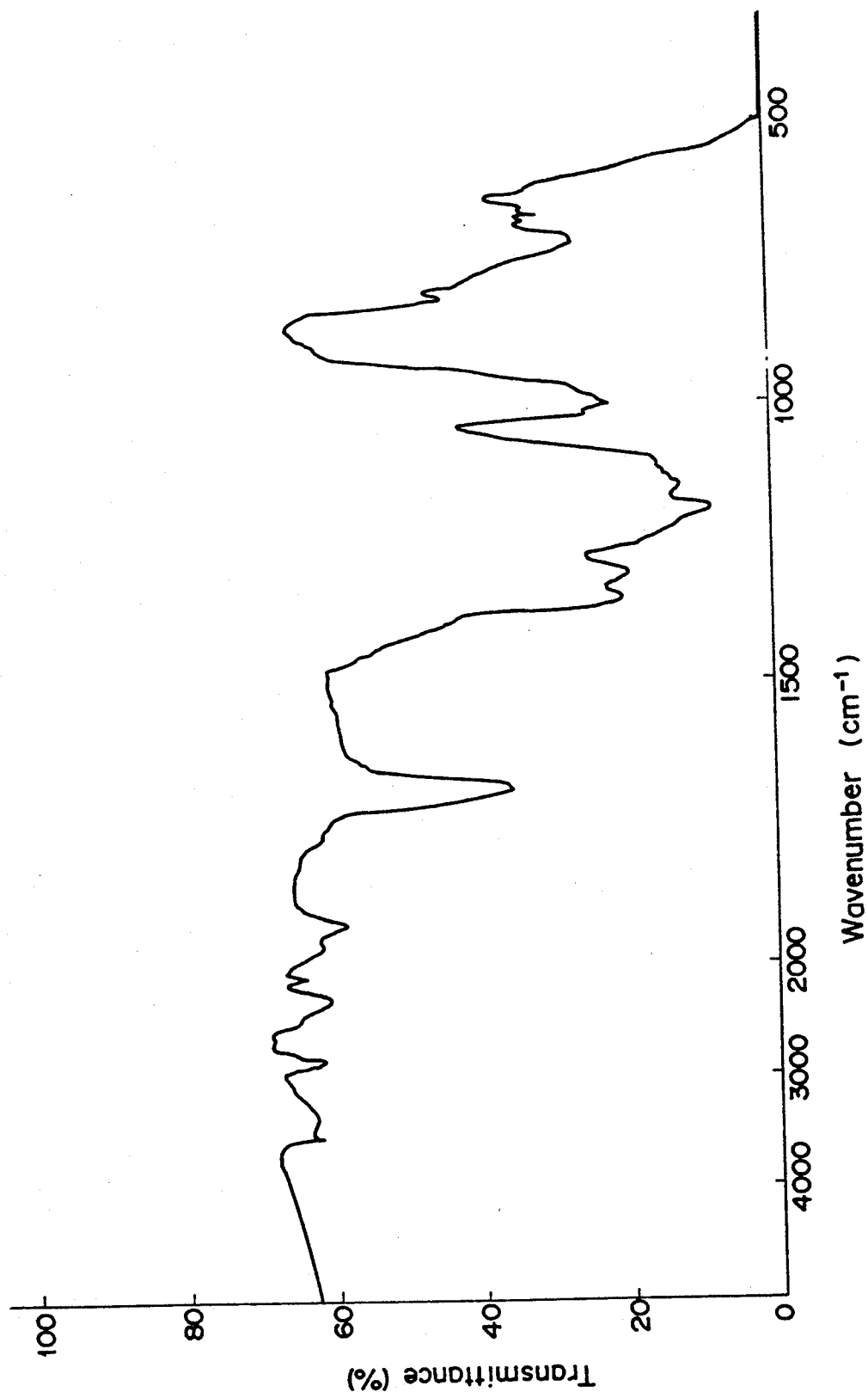
Figure

FLUORINE-CONTAINING POLYETHER AND NONIONIC SURFACTANT COMPRISING THE SAME

This application is a divisional of copending application Ser. No. 07/556,419, filed on Jul. 14, 1990, which is a continuation-in-part of application Ser. No. 07/340,481 filed on Apr. 19, 1989, now abandoned, the entire contents of which are hereby incorporated by reference.

BACKGROUND OF THE INVENTION

1. Field of the Invention

The present invention relates to a novel fluorine-containing polyether and a nonionic surfactant comprising the same fluorine-containing polyether.

2. Description of the Related Art

Since a perfluoroalkyl polyether has high electrical insulation and non-flammability properties, it is used in various applications, particularly in an electrical application. However, the perfluoroalkyl polyether is statically charged to collect dust. Therefore, a surfactant which can be used as an antistatic agent in the perfluoroalkyl polyether is required. However, conventional surfactants are not compatible with the perfluoroalkyl polyether and cannot be used as the antistatic agent.

A fluorine-containing polyether which is used as a lubricant is developed. Japanese Patent Kokai Publication Nos. 25825/1988 and 27599/1988 disclose a fluorine-containing polyether used as a lubricant for a magnetic disc. However, this polyether has perfluoromethyl branches in the molecule and has insufficient durability.

SUMMARY OF THE INVENTION

An object of the present invention is to provide a fluorine-containing polyether which can be used as the surfactant compatible with the perfluoroalkyl polyether.

Another object of the present invention is to provide a fluorine-containing polyether which has good durability when used in a magnetic recording medium.

These and other objects are achieved by a fluorine-containing polyether of the formula:

$$R_f\text{—X—A} \quad (I)$$

or $$\text{A—X—}R'_f\text{—X—A} \quad (II)$$

wherein $R_f$ is a linear group containing at least one repeating unit of the formula:

$$-CF_2CF_2CF_2O-$$

$R'_f$ is a linear group containing at least one repeating unit selected from the group consisting of a repeating unit of the formula:

$$-CF_2CF_2CF_2O- \quad (a)$$

a repeating unit of the formula:

$$-CF_2CF_2O- \quad (b)$$

and a repeating unit of the formula:

$$-CF_2O- \quad (c)$$

provided that at least one of the repeating units (a) and (b) is contained and the total number of the repeating unit (a), (b) and (c) is at least three, X is $-CF_2COO-$, $-C_2F_4COO-$ or $-CF_2CF_2-$ and A is a group containing a polyalkylene glycol group.

Also, the present invention provides a nonionic surfactant comprising said fluorine-containing polyether.

BRIEF DESCRIPTION OF THE DRAWING

Figure is an IR chart of the fluorine-containing polyether of Example 1.

DETAILED DESCRIPTION OF THE INVENTION

The term "linear group" in the present invention is intended to mean that the molecule has no branch such as a perfluoromethyl group.

The $R_f$ group is, for example, $$F(CF_2CF_2CF_2O)_m-$$

wherein m is 2 to 200.

The $R'_f$ group is, for example, $$-(OCF_2CF_2)_m(OCF_2)_nO-$$

wherein m is 1 to 200 and n is 0 to 200, and $$-O(CF_2CF_2CF_2O)_mCF_2CF_2CF_2CF_2CF_2CF_2(OCF_2CF_2CF_2)_mO-$$

wherein m is 1 to 200.

an alkylene glycol which forms the polyalkylene glycol group in the A group may be ethylene glycol or propylene glycol. The polyalkylene glycol group contains at least one repeating unit selected from the group consisting of a repeating unit of the formula:

$$-C_2H_4O-$$

and a repeating unit of the formula:

$$-C_3H_6O-$$

provided that total number of said repeating units is 2 to 500. The repeating unit: $-C_3H_6O-$ includes $-CH_2CH_2CH_2O-$ and $-CH(CH_3)CH_2O-$. The repeating unit: $-C_2H_4O-$ is usually $-CH_2CH_2O-$.

The A group is, for example, $$-(CH_2CH_2O)_mCH_3$$

wherein m is 2 to 500, $$-(CH_2CH_2O)_mH$$

wherein m is 2 to 500, or $$-CH_2CH_2O(\overset{CH_3}{\underset{|}{C}H}CH_2O)_mH$$

wherein m is 2 to 500.

Specific examples of the fluorine-containing polyethers (I) and (II) are $$F(CF_2CF_2CF_2O)_mCF_2CF_2COO(CH_2CH_2O)_nCH_3$$

wherein m is 2 to 200, preferably 9 on the average and n is to 2 to 500, preferably 9 on the average, $$CH_3O(CH_2CH_2O)_l\overset{O}{\underset{\|}{C}}CF_2(OCF_2CF_2)_m$$

$$(OCF_2)_nOCF_2\overset{O}{\underset{\|}{C}}O(CH_2CH_2O)_lCH_3$$

wherein m+n is 3 to 200, preferably 10 on the average and l is 2 to 500, preferably 9 on the average, $$-[CF_2CF_2CF_2-(OCF_2CF_2CF_2)_m-OCF_2CF_2-(CH_2CH_2O)_n-CH_3]_2$$

wherein m is 2 to 200, preferably 10 on the average and n is 2 to 500, preferably 9 on the average, and $$F(CF_2CF_2CF_2O)_mCF_2CF_2CH_2CH_2O(\overset{CH_3}{\underset{|}{C}H}CH_2O)_nH$$

wherein m is 2 to 200, preferably 20 on the average and n is 2 to 500, preferably 10 on the average.

The fluorine-containing polyether (I) can be prepared by reacting a fluorine-containing compound of the formula:

$$R_f-X-H$$

with a compound of the formula:

$$HO-A$$

or reacting a fluorine-containing compound of the formula:

$$R_f-X-I$$

with a compound of the formula:

$$M-A$$

wherein A, $R_f$ and X are the same as described above and M is an alkaline metal. The fluorine-containing polyether (II) can be prepared by reacting a fluorine-containing compound of the formula:

$$H-X-R'_f-X-H$$

with a compound of the formula:

$$HO-A$$

wherein A, $R'_f$ and X are the same as described above. The reaction is usually carried out at a temperature of 20° to 150° C. for 1 to 10 hours.

The fluorine-containing polyether according to the present invention is water-soluble and can be used as a nonionic surfactant.

The nonionic surfactant according to the present invention can be used as an antistatic agent, a surfactant for polymerization, car wax, an additive for film and a lubricant.

The fluorine-containing polyether according to the present invention is compatible with a perfluoroalkyl polyether and thus can be used as an antistatic agent for the perfluoroalkyl polyether. It can improve properties of a resin surface when used as an additive for resin, particularly a resin film.

The fluorine-containing polyether according to the present invention has good durability and stable lubricity when used as a lubricant for a magnetic recording medium.

PREFERRED EMBODIMENTS OF THE INVENTION

The present invention is illustrated by following Examples.

EXAMPLE 1

To the fluorine-containing carboxylic acid:

$$F(CF_2CF_2CF_2O)_mCF_2CF_2COOH$$

wherein m is 30 on the average (51.3 g, 10 mmol), the polyethylene glycol methyl ether:

$$CH_3(OCH_2CH_2)_nOCH_2CH_2OH$$

wherein n is 8 on the average (10 g, 25 mmol) (Uniox 400 manufactured by Nippon oil & fats Co., Ltd.) was added and stirred. Then, concentrated sulfuric acid (5 ml) was added and the reaction was carried out at 100° C. for 6 hours while stirring. The completion of the reaction was confirmed by disappearance of the absorption peak at 1780 cm$^{-1}$ for the carboxylic acid and appearance of the absorption peak at 1700 cm$^{-1}$ for the ester linkage in IR analysis. After the completion of the reaction, the reaction product was washed with a 2% aqueous solution of NaHCO$_3$ (50 ml) twice. A lower phase was separated and filtrated through a filter having a pore diameter of 0.2 μm to obtain the fluorine-containing polyether:

$$F(CF_2CF_2CF_2O)_mCF_2CF_2COO(CH_2CH_2O)_{n+1}CH_3$$

wherein m is 30 and n is 8 on the average. Yield: 47 g (87%).

The IR chart of the resultant fluorine-containing polyether is shown in Figure.

EXAMPLE 2

A perfluoropolyether (Demnum S-65 manufactured by Daikin Industries Ltd.) (10 g) was mixed with the fluorine-containing polyether:

$$F(CF_2CF_2CF_2O)_mCF_2CF_2COO(CH_2CH_2O)_{n+1}CH_3$$

wherein m is 30 and n is 8 on the average prepared in Example 1 (0.3g), and then dissolved in trichlorotrifluoroethane (100 g). A slide glass (15 cm×5 cm) was dipped in the solution, dried in the air to form a film having a thickness of not less than 10 μm on the slide glass. A potential was measured by a potentiometer, while violently rubbing the film with a styrene resin. The potential difference was 0 V.

COMPARATIVE EXAMPLE

A film was formed and a potential difference was measured in the same manner as in Example 2 but the fluorine-containing polyether was not used. The potential difference was 400 V.

EXPERIMENT

Durability of the polyether of the present invention and a comparative polyether is determined.

As the comparative polyether, a compound in Example 1 of Japanese Patent Kokai Publication No. 27599/1988, namely a compound of the formula:

$$CF_3(CFCF_2O)_{14}CFCO(OC_2H_4)_4OH \quad (1)$$
$$\phantom{CF_3(}|\phantom{CFCF_2O)_{14}}|$$
$$\phantom{CF_3(}CF_3\phantom{CFCF_2O)_{14}}CF_3$$

(Molecular weight: 2714)

was used.

As the polyether of the present invention, the compound of the formula:

$$F(CF_2CF_2CF_2O)_{14}CF_2CF_2CO(OC_2H_4)_4OH \quad (2)$$

(Molecular weight: 2664)

was used.

Each of the compounds (1) and (2) was dissolved in trichlorotrifluoroethane to prepare a 0.1% by weight solution. A magnetic disk was dipped in the solution and dried. Durability was tested by using a CSS tester.

The results are as follows

| CSS test times | |
|---|---|
| Compound (1) | 3,000 |
| Compound (2) | 10,000 |

As is clear from the results, the compound of the present invention has better durability than the comparative compound.

What is claimed is:

1. A fluorine-containing polyether of the formula:

$$F(CF_2CF_2CF_2O)_mCF_2CF_2COO(CH_2CH_2O)_nCH_3$$

wherein m is 2 to 200 and n is 2 to 500 or $$CH_3O(CH_2CH_2O)_l\overset{O}{\underset{\|}{C}}CF_2(OCF_2CF_2)_m$$

$$(OCF_2)_nOCF_2\overset{O}{\underset{\|}{C}}O(CH_2CH_2O)_lCH_3$$

wherein m+n is 3 to 200 and l is 2 to 500.

2. A fluorine-containing polyether of the formula:

$$F(CF_2CF_2CF_2O)_mCF_2CF_2COO(CH_2CH_2O)_nCH_3$$

wherein m is 9 and n is 9 or $$CH_3O(CH_2CH_2O)_l\overset{O}{\underset{\|}{C}}CF_2(OCF_2CF_2)_m$$

$$(OCF_2)_nOCF_2\overset{O}{\underset{\|}{C}}O(CH_2CH_2O)_lCH_3$$

wherein m+n is 10 and l is 9.

* * * * *